US006284744B1

(12) United States Patent
Di Zerega

(10) Patent No.: US 6,284,744 B1
(45) Date of Patent: Sep. 4, 2001

(54) PERITONEAL INDUCED MEDICAMENTS

(76) Inventor: Gere S. Di Zerega, 420 San Juan Pl., Pasadena, CA (US) 91107

(*) Notice: Subject to any disclaimer, the term of this patent is extended or adjusted under 35 U.S.C. 154(b) by 0 days.

(21) Appl. No.: 07/884,218

(22) Filed: May 11, 1992

Related U.S. Application Data

(63) Continuation of application No. 07/479,111, filed on Feb. 13, 1990, now abandoned.

(51) Int. Cl.[7] ................................................ A61K 31/70
(52) U.S. Cl. ........................... 514/54; 514/23; 514/24; 514/210; 514/247; 514/613; 524/788
(58) Field of Search ........................... 514/23, 24, 54, 514/210, 247, 613; 424/488

(56) References Cited

U.S. PATENT DOCUMENTS

| | | | |
|---|---|---|---|
| 4,736,024 | * 4/1988 | Della Valle et al. | 536/54 |
| 4,746,504 | * 5/1988 | Nimrod et al. | 514/54 |
| 4,782,046 | * 11/1988 | Brown et al. | 514/54 |
| 4,851,521 | * 7/1989 | Della Valle et al. | 514/54 |
| 4,889,722 | * 12/1989 | Sheffield et al. | 514/8 |
| 4,920,104 | * 4/1990 | De Vore et al. | 514/54 |
| 5,080,893 | * 1/1992 | Goldberg et al. | 514/57 |
| 5,140,016 | * 8/1992 | Goldberg et al. | 514/54 |

FOREIGN PATENT DOCUMENTS

| | | |
|---|---|---|
| 0138572 | * 4/1985 | (EP) . |
| 0769287 | * 3/1957 | (GB) . |
| 60-84225 | * 5/1985 | (JP) . |
| WO914058 | 4/1991 | (WO) . |

OTHER PUBLICATIONS

The Merck Index, 10th Ed. M. Windholz et al, Eds. pp. 335, 499 and 1075–1076 (1983).*

O. Boudoris, et al., "Effet synergique due Dextran 70 a 32% et d'un antibiotique dans la prevention des adherences peritoneals", *Journal of Clinical Pharmacology* (1992): 160–164.

Dunn, et al., "The Adjuvant Effect of Peritoneal Fluid in Experimental Peritonitis," *Annals of Surgery* (1984): 37–43.

Cohn, Z.A. and Morse, S.I., "Interactions Between Rabbit *Polymorphonuclear Leucocytes* and Staphylococci," *Journal of Experimental Medicine* 110 (1959) : 419–443.

Hirsch, J.G. and Church, A.B., "Studies of Phagocytosis of Group A Streptoccocci by *Polymorphonuclear Leucocytes* In Vitro,"*The Journal of Experimental Medicine* 111 (1960) : 309–322.

Jenkin, C. and Benacerraf, J., "In Vitro Studies on the Interaction Between Mouse Peritoneal Macrophages and Strains of Salmonella and *Escherichia Coli*," *The Journal of Experimental Medicine* (1960) : 403–417.

Roberts, R.B., "The Interaction In Vitro Between Group B Meningococci and Rabbit *Polymorphonuclear Leukocytes*," *The Journal of Experimental Medicine* (1967) : 795–817.

Howard, et al., "Surgical Infectious Disease" 2nd ed., p. 160, Appleton and Lange, East Norwalk, Conn., 1988.

Gere S. diZerega, et al.; *The Peritoneum*; cover page (1 page), publisher page (1 page), table of contents (3 pages), pp. 1–25, pp. 26–56, p. 91, pp. 156–158, pp. 158–160, pp. 195–199, pp. 307–308, pp. 308–309, pp. 274–306, pp. 307–369, conclusions pp. 22, 23, 93, 203, 264, 300 and 356, and index pp. 371–378.

Harold Ellis; "The Cause And Prevention of Postoperative Intraperitoneal Adhesions"; (1971); pp. 497–511.

Kathleen Rodgers, et al.; Draft "Reduction of Intraperitoneal Abscess Formation After Administration of Antibiotics In Hyaluronic Acid"; (yet to be published); pp. 1–28.

* cited by examiner

*Primary Examiner*—Elli Peselev
(74) *Attorney, Agent, or Firm*—Christie, Parker & Hale, LLP

(57) ABSTRACT

A solution of hyaluronic acid and water-soluble salts thereof in a pharmaceutically acceptable media in which the hyaluronic acid concentration is at least about 0.4% by weight based on the weight of the solution and the solution having a viscosity at 25° C. of from about 500 to about 10,000 centipoises, serving as a carrier for medicaments to the peritoneal cavity.

4 Claims, No Drawings

PERITONEAL INDUCED MEDICAMENTS

CROSS-REFERENCE TO RELATED APPLICATIONS

This is a continuation of application Ser. No. 07/479,111 filed Feb. 13, 1990 now abandoned.

BACKGROUND OF THE INVENTION

The present invention is directed to the use of hyaluronic acid ("HA" herein), or a water soluble salt thereof such as sodium hyaluronate, in a readily flowable medium, as a carrier for direct introduction of medicaments such as antibiotics to the peritoneal cavity for enhanced and effective healing following surgical trauma. The invention is particularly directed to preventing or minimizing interperitoneal infections. Many mammalian surgical procedures involve invasion of the peritoneal cavity. They occur with attendant introduction of bacteria. The current procedure has been to close the surgical opening following completion of the surgical procedure with contemporaneous or subsequent combatting of bacteria with intravenous antibiotic treatment. Treatment may last for periods ranging from five to seven days. During this period of time, scar tissue or adhesions can develop along with other discomforting effects such as localized pain, obstruction of the bowel and the like.

Sera has been relied on to carry the intravenously introduced antibiotic to the situs of the trauma. Sera does a poor job, however, because bacteria retards sera flow and is present in the incision area in high concentration combatting the efficacy of the antibiotic. It would be more effective, faster and more efficient if the antibiotic could be introduced directly to the peritoneal cavity at the time of surgery or for short periods thereafter. The difficulty, however, is that no vehicle currently is known which would allow direct administration to the peritoneal cavity without attendant almost immediate loss, i.e. within an hour, of the introduced antibiotic through the wall of the cavity by absorption or other means.

SUMMARY OF THE INVENTION

According to the present invention, hyaluronic acid is utilized in solution, in a pharmaceutically acceptable media, typically a sterile, readily flowable isotonic aqueous solution, as a carrier for medicaments, typically antibiotics, to enable direct application within the peritoneal cavity of an effective amount of such antibiotic from a time beginning at surgery and, if necessary, for a longer period of time, to enable localized treatment to combat or inhibit infection. Preferred, however, and most convenient, is to administer the carrier as a single application at the conclusion of the surgical procedure just prior to closing, with the solution applied to the site of the infection and adjacent tissue, with enough solution used so that the intraperitoneal circulation within the cavity, as a consequence of migration, will occur. Thus, direct coating of the surfaces of the peritoneal cavity are assured and less infection and discomfort and more rapid and complete healing will occur.

The hyaluronic acid solution of the instant invention is provided in a sterilized, easily pourable solutions having an equivalent hyaluronic acid concentration of at least about 0.4% by weight based on the weight of the solution of hyaluronic acid, or a water soluble salt thereof, said solution having a viscosity of 25° C. within a range of 500 to 10,000 centipoise, preferably from about 500 to about 6,000 centipoise. The hyaluronic acid, or salt thereof, employed in the invention preferably has a molecular weight of from about 500,000 or less to about 2.5 million or more, preferably from about 1 to about 1.5 million. In the practice of the invention, the hyaluronic acid solution and the medicament is applied topically to the peritoneal cavity to provide an effective amount of medicament to a mammal responsive to the medicament for a period of time beginning at the time of surgery along, if desired, with continuing application for a period of time sufficient to inhibit or prevent infection. It is preferred to administer the solution in a single application, such as by lavage, at the conclusion of the surgical procedure just prior to closing. In practice of the instant invention, the combat of infection is localized to the peritoneal cavity, enhancing control of infection and the speed of healing.

DETAILED DESCRIPTION

The present invention provides solutions for use in combatting potential infections of the peritoneal cavity and methods for the use thereof.

The solutions contemplated to be used in accordance with the present invention are based on hyaluronic acid ("HA" herein) or a soluble salt thereof, such as sodium hyalurate in a pharmaceutically acceptable media, sterile, flowable, e.g. readily pourable, typically isotonic media, preferably an aqueous media, in which the hyaluronic acid concentration is at least about 0.4 per cent by weight based on the weight of the solution, the solutions having a viscosity of 25° C. of about 500 to about 10,000 centipoise measured at a shear rate of 1 sec.$^{-1}$ using a cone and plate viscometer, preferably having a viscosity of about 500 to about 6,000 centipoise at 25° C. Hyaluronic acid is a naturally occurring substance produced by mammals, or artificially generated, and has a molecular weight sufficiently high such that it cannot be absorbed from the peritoneal cavity. Typically, hyaluronic acid has a molecular weight from about 500,000 to about 2.5 million or more, preferably from about 1 to about 1.5 million. Molecular weight is determined by the intrinsic viscosity method of Laurent et al., *Biochimica and Biophysica*, Acta, 42 476–485, 1960, incorporated herein by reference.

The hyaluronic acid and medicament are administrated in a sterilized isotonic formulation of a pharmaceutically acceptable carrier or a diluent vehicle such as a phosphate buffered in a saline solution or isotonic saline solution. Preferably the pH of the solution is physiologically acceptable and typically within the range of about 7.0 to about 7.6. Sterilization may be achieved by an aseptic preparation, filtration through a filter having a pore size of about 0.2 micron or less, or other acceptable means.

The hyaluronic acid is normally provided as a solid in powder form and is simply mixed with an appropriate amount of the carrier solution, dissolved by agitation, then sterilized. As required, sterilization of the container may be achieved by standard procedure such as electron beam radiation or ethylene oxide treatment.

There is added at the time of formulation, or at the time of use, an ingredient to be used in combating infections of the peritoneal cavity including, but not limited to, antibiotics such as piperacillin, clindamycin, doxycycline, and the like. There is formed an easily pourable solution which may be administered to the site of the incision or surgical trauma by any convenient means such as lavage, by catheter, or by coating the site from any convenient means of application. It is administered in an amount to provide a dose on application, or over a period of time, with sufficient wound healing force. As a minimum, there is applied an amount sufficient to combat infection for at least the initial stages of wound healing. Typically, a single topical application of the hyaluronic acid solution is all that is required. Application over a period of time may also be used. When a single application is utilized, the most convenient time for such administration is just prior to closing at the end of the operative procedure. The amount applied is typically sufficient to coat the traumatized tissue with a thin coating of the hyaluronic acid solution. Preferably, however, the solution is used in a quantity sufficient to coat all the surfaces in the peritoneal cavity. While dosage will vary depending on individual characteristics, including the size of the patient and severity or extent of the trauma, in most cases a coat of about 150 millimeters of sterile solution is sufficient for the average size human.

In any event, it is preferred that sufficient solution be used so that peritoneal recirculation enables the solution to migrate to all surfaces within the cavity to achieve an effective, contained coating of the solution and medicament.

In a preferred fashion, the solution is applied to the exact side of the infection and onto adjacent tissue. Again, whether administration is continued beyond the term of the surgical procedure will depend upon the surgical procedure and the potential extent of infection. The hyaluronic acid serves as a media which maintains the medication at the site of the trauma within the peritoneal cavity and by the migrations throughout the area so as to ensure combating of infection by bacteria and the like and thorough healing of the trauma site.

While in no way limiting, the following describes evaluation of a mammal's (female Sprague-Dawley rat each weighing between 150–200 gms) ability to survive a capsule induced source of infection for 11 days. Compared were rats with no treatment to curb infection to rats treated with an antibiotic applied as such to the peritoneal cavity or an antibiotic administered with hyaluronic acid (HA) in salt form to the peritoneal cavity.

For an evaluation, the capsule was prepared by mixing the fecal contents and feces from rats fed hamburger for 2 weeks in a 1:1 weight ratio with a peptone yeast broth glucose (Scott Laboratories) and 10% by weight barium sulfate. 24 ul of the diluted fecal material was added to a 0.5 ml No. 1 gelatin capsule (Eli Lilly and Company), and this capsule was placed in a second larger No. 00 double walled gelatin capsule (Eli Lilly and Company).

All rats which underwent testing were prepared by standardized shaving of the abdomen using electric animal clippers and Betadine preparation of the abdomen prior to a midline laparotomy under ketamine HCl and xylazine (Rompum) anesthesia. The capsule was placed in the peritoneum on the right side through the midline incision. Following implantation, the cavity was closed or varying amounts of test material were placed under and over the capsule in the peritoneal cavity. The abdominal wall was closed using 5-0 Ethilon suture, and the subcutaneous tissue and skin was closed using a continuous subcuticular pattern with 5-0 polyglactin 910 (VICRYL) suture.

Following surgery, the rats were observed twice daily for signs of morbidity/mortality. Their health status was evaluated on the basis of food and water consumption and excretion.

Diet consisted of Purina Rodent Laboratory Chow (Ralston Purina Corp.) and water fed ad libitum except during the postsurgical recovery period.

The rats were handled in accordance with the USC Vivarium Protocol 6021, and the standards listed in the *Guide for the Care and Use of Laboratory Animals*, NIH Publication No. 85-23, revised 1985.

The rats which died during the 11 day observation period were necropsied to confirm the presence of acute bacterial infection. Necropsy was limited to the external surfaces and the abdominal and thoracic viscera.

The rats that survived the acute infection were sacrificed at 11 days following surgery. Each rat was examined for transcutaneous palpability of the abscesses. Upon opening, the odor of the peritoneal cavity was noted. The animal was examined for splenomegaly, and seven areas of the peritoneum examined for abscess formation. These areas include the liver, spleen, abdominal wall, retrohepatic gutter, colonic gutter, bowel, and omentum. The presence of abscesses was noted.

The abscesses were scored at each site as follows:

0—No abscesses present at site 0.5+—One very small abscess present at site

1+—Several small abscesses present at site

2+—Medium to large abscesses present at site

3+—One very large abscess present at site

The scoring was performed in a blind, randomized fashion by two separate observers and the scores were recorded separately. If there was a disagreement between the two observers as to the score at a particular site, the most severe score recorded was used in the evaluation.

Previous studies had established that the capsuled contents led to death in 10 to 15% of the rats and severe peritoneal infection and abscess formation within 11 days of implantation of the capsule. Table 1 shows the percent of animals, compared to normal, with abscesses which developed, in the same time periods, in rats which survived the treatment.

Abscess is a local collection of pus indicating a persistence of infection. For Table 1, piperacillin, clindamycin or doxycycline were applied in a respective concentration of 15, 1 or 0.28 mg per rat alone or admixed with 1 ml of a 1,000 cps hyaluronic acid (HA) solution.

Table 2 shows the results of the studies on the rats showing death (LDSD study) and number of abscesses and rating of abscess. A + sign means between the rating given and the next highest rating.

TABLE 1

% of Average Amount of Abscesses

|  | Antibiotic | HA + Antibiotic |
|---|---|---|
| Piperacillin | | |
| Liver | 95% | 47% |
| Abdomen | 122% | 61% |
| Bowel and Guts | 56% | 9% |
| Omentum | 96% | 65% |
| Clindamycin | | |
| Liver | 100% | 61% |
| Abdomen | 127% | 20% |
| Bowel and Guts | 137% | 4% |
| Omentum | 96% | 65% |
| Doxycycline | | |
| Liver | 100% | 58% |
| Abdomen | 150% | 50% |
| Bowel and Guts | 118% | 31% |
| Omentum | 115% | 78% |

TABLE 2

|  | Treatment | | | |
| --- | --- | --- | --- | --- |
|  | Control (none) | Piperacillin 15 mg/rat | Clindamycin 1 mg/rat | Doxycycline 0.28 mg/rat |
| Death: | 5/10 | 0/10 | 2/10 | 3/10 |
| Abscesses: | | | | |
| Liver: | 1/5 2+ | 4/10 1+ | 7/8 2+ | 1/7 1+ |
|  | 1/5 3+ | 6/10 2+ | 1/8 3+ | 5/7 2+ |
|  | 3/5 4+ | | | 1/7 3+ |
| Abd. Wall | 3/5 3+ | 1/10 – | 4/8 – | 1/7 – |
|  | 2/5 4+ | 3/10 1+ | 3/8 1+ | 2/7 1+ |
|  | | 6/10 3+ | 1/8 3+ | 2/7 2+ |
|  | | | | 2/7 3+ |
| Bowel & | 2/5 – | 9/10 – | 7/8 – | 5/7 – |
| Guts | 1/5 3+ | 1/10 2+ | 1/8 1+ | 1/7 2+ |
|  | 2/5 4+ | | | 1/7 3+ |
| Omentum | 1/5 2+ | 2/10 1+ | 1/8 1+ | 1/7 1+ |
|  | 2/5 3+ | 5/10 2+ | 5/8 2+ | 1/7 2+ |
|  | 2/5 4+ | 3/10 3+ | 2/8 3+ | 5/7 3+ |

The invention employs hyaluronic acid (sometimes referred to as "HA") or a water-soluble salt thereof (such as sodium hyaluronate) in a sterile, isotonic, easily pourable aqueous solution having a concentration of at least about 0.4 weight percent (based on weight of the entire solution) of hyaluronic acid or water-soluble salt thereof, and having a viscosity at 25° C. within the range of from about 500 to about 10,000 centipoise (measured at a shear rate of 1 sec$^{-1}$ in a cone and plate viscometer). Preferably, the hyaluronic acid solution employed in the invention has a viscosity below about 5,000 centipoise at 25° C. The hyaluronic acid (or water-soluble salt thereof) employed in the invention preferably has a molecular weight of from about five hundred thousand to about one and one-half million. However, higher molecular weight hyaluronic acid having a molecular weight of up to, for example, two and one-half million, can also be used in the invention. The molecular weight is determined by the intrinsic viscosity method of Laurent et al., Biochimica Et Biophysica Acta, 42, 476–485 (1960).

In accordance with the method of the invention, the sterile, easily pourable, isotonic hyaluronic acid solution is applied topically to the peritoneal cavity in effective amounts for a period of time beginning after surgery and continuing for a period of time sufficient to inhibit infection. It is preferred and most convenient to administer the hyaluronic acid in a single application such as a lavage at the conclusion of the surgical procedure just prior to closing.

In the preferred mode of carrying out the invention, the HA solution is applied to the exact site of the infection and to the adjacent tissue, but enough of the solution is used so that intraperitoneal circulation within the peritoneal cavity will cause migration of the solution such that substantially all the surfaces within the peritoneal cavity will be coated with the solution.

The sterile, easily pourable, isotonic HA solution may be administered to the site of surgical trauma by any convenient means such as, for example, by lavage, by catheter, by coating directly on the site from an appropriate container/applicator, or by any other convenient means. Migration of fluids occurs naturally within the peritoneal cavity, and the use of the easily pourable hyaluronic acid solutions of this invention facilitates such intraperitoneal migration.

The HA solution is administered in a sterile, isotonic formulation in a pharmaceutically acceptable carrier or diluent vehicle such as phosphate buffered saline ("PBS") or isotonic saline. Preferably, the pH of the solution is physiological, i.e., within the range of from about 7.0 to 7.6. Sterilization of the formulation may be accomplished by filtration through a filter whose pore size is 0.2 micron or smaller, or by other acceptable means.

The sterile, easily pourable, isotonic hyaluronic solutions used in the invention are prepared by procedures that are analogous to those that are known in the art. For instance, the hyaluronic acid (preferably as sodium hyaluronate), in powder form, may simply be mixed with the appropriate quantity of isotonic aqueous liquid, such as phosphate buffered saline or isotonic saline, and dissolved by stirring or other agitation. Sterilization may be effected by filtering through a 0.2 micron filter or by aseptic preparation. Secondary sterilization of the container may be effected by standard procedures such as by electron beam irradiation or ethylene oxide treatment.

The sterile, easily pourable, isotonic hyaluronic acid solution is delivered to the site of infection in the peritoneal cavity in effective quantities over the desired period of time, which period may vary from patient to patient, with the type of severity of the trauma, with the location of the traumatized tissue within the peritoneal cavity, or the like.

Referring to the question of the effective dose of HA solution when used in the invention, the HA solution is used in a quantity sufficient to coat the traumatized tissue with a thin coating of HA solution. Preferably, the HA solution is used in a quantity sufficient to coat all the surfaces in the peritoneal cavity. The exact quantity needed may vary in individual cases, depending on the size of the patient, the severity and/or extent of the trauma, and the like. However, in most cases, a dose of about 150 ml of sterile, easily pourable, isotonic solution of HA is sufficient for an average sized human.

The HA is administered to the site of surgical trauma within the peritoneal cavity topically. Such topical administration can be by lavage, dripping on the site from a syringe or other suitable container/applicator, by catheter administration, or the like. The exact method of administration chosen has not been found to be critical, as long as an effective dose is administered over the period beginning before significant wound healing has occurred and continuing for at least the initial stages of wound healing. As will be illustrated in the Examples, a single application of the hyaluronic acid solution is efficacious in most cases. With such single applications, the time period over which the hyaluronic acid is in effective contact with the site of surgical trauma may be very short, e.g., as little as, for example, about one to three hours. When the method of the invention is carried out by a single application of the low viscosity hyaluronic acid solution, the most convenient time for such administration is just prior to closing at the end of an operative procedure.

What is claimed is:

1. A method for combating infections of the peritoneal cavity which comprises providing to the peritoneal cavity of a mammal undergoing surgery, a solution of a medicament and an hyaluronic acid compound selected from hyaluronic acid and water-soluble salts thereof in a sterile, isotonic, flowable pharmaceutically acceptable media in which the hyaluronic acid compound is present in a concentration of at least about 0.4% by weight based on the weight of the solution, said solution having a viscosity at 25° C. of from about 500 to about 10,000 centipoise, said hyaluronic acid compound acting to retain the introduced medicament in the peritoneal cavity, the amount of solution applied being sufficient to at least coat traumatized tissue and up to an amount sufficient to coat the peritoneal cavity, said solution being applied as a single application at closing of the peritoneal cavity at the end of the operative procedure.

2. A method as claimed in claim 1 in which the dosage is about 150 ml of solution.

3. A method as claimed in claim 1 in which the medicament is an antibiotic.

4. A method as claimed in claim 3 in which the antibiotic is selected from the group consisting of piperacillin, clindamycin and doxycycline.

* * * * *